(12) United States Patent
Golenberg et al.

(10) Patent No.: US 12,263,327 B2
(45) Date of Patent: Apr. 1, 2025

(54) SYNERGISTIC FEATURES AND FUNCTIONS RELATED TO OPERATION OF A MEDICATION DELIVERY SYSTEM AND A MEAL TRANSACTION APPLICATION

(71) Applicant: MEDTRONIC MINIMED, INC., Northridge, CA (US)

(72) Inventors: Lavie Golenberg, Sherman Oaks, CA (US); Maria Diana Miller, Santa Rosa Valley, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 617 days.

(21) Appl. No.: 17/096,845

(22) Filed: Nov. 12, 2020

(65) Prior Publication Data
US 2021/0146045 A1 May 20, 2021

Related U.S. Application Data

(60) Provisional application No. 62/947,988, filed on Dec. 13, 2019, provisional application No. 62/935,411, filed on Nov. 14, 2019.

(51) Int. Cl.
*A61M 5/172* (2006.01)
*A61M 5/142* (2006.01)

(52) U.S. Cl.
CPC ........ *A61M 5/172* (2013.01); *A61M 5/14248* (2013.01); *A61M 2205/502* (2013.01); *A61M 2205/52* (2013.01); *A61M 2205/583* (2013.01); *A61M 2205/587* (2013.01); *A61M 2205/8206* (2013.01); *A61M 2230/201* (2013.01); *A61M 2230/63* (2013.01)

(58) Field of Classification Search
CPC .............. A61M 5/172; A61M 5/14248; A61M 5/1723; A61M 5/24; A61M 2205/502;
(Continued)

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| CN | 101326526 A | 12/2008 |
| CN | 102281817 A | 12/2011 |

(Continued)

OTHER PUBLICATIONS

PCT International Search Report and Written Opinion for International Application No. PCT/US2020/064693 mailed on Mar. 18, 2021 (13 pages).

(Continued)

*Primary Examiner* — Kevin C Sirmons
*Assistant Examiner* — Leah J Swanson
(74) *Attorney, Agent, or Firm* — Weaver Austin Villeneuve & Sampson LLP

(57) ABSTRACT

The subject matter of this disclosure generally relates to a medical device system and related methodologies that leverage data associated with the use of a meal transaction application, such as an application for ordering food delivery. Data generated by the meal transaction application can be leveraged by a patient care system or application for purposes of diet or calorie logging. Alternatively or additionally, the meal transaction data can be leveraged for purposes of controlling the administration of therapy by a medication delivery system, such as an insulin infusion pump.

22 Claims, 8 Drawing Sheets

(58) Field of Classification Search
CPC ...... A61M 2205/583; A61M 2205/587; A61M 2205/8206; A61M 2230/201; A61M 2230/63; G16H 20/17; G16H 40/63; G16H 50/20

See application file for complete search history.

(56) References Cited

U.S. PATENT DOCUMENTS

| | | | |
|---|---|---|---|
| 4,755,173 A | 7/1988 | Konopka et al. |
| 5,080,653 A | 1/1992 | Voss et al. |
| 5,097,122 A | 3/1992 | Colman et al. |
| 5,391,250 A | 2/1995 | Cheney, II et al. |
| 5,485,408 A | 1/1996 | Blomquist |
| 5,505,709 A | 4/1996 | Funderburk et al. |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,485,465 B2 | 11/2002 | Moberg et al. |
| 6,544,212 B2 | 4/2003 | Galley et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,659,980 B2 | 12/2003 | Moberg et al. |
| 6,736,797 B1 | 5/2004 | Larsen et al. |
| 6,749,587 B2 | 6/2004 | Flaherty |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,817,990 B2 | 11/2004 | Yap et al. |
| 6,932,584 B2 | 8/2005 | Gray et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Stoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,771,251 B2 | 7/2014 | Ruchti et al. |
| 9,042,596 B2 | 5/2015 | Connor |
| 9,110,510 B2 | 8/2015 | Moore et al. |
| 9,254,099 B2 | 2/2016 | Connor |
| 9,396,369 B1 | 7/2016 | Whitehurst et al. |
| 9,442,100 B2 | 9/2016 | Connor |
| 9,529,385 B2 | 12/2016 | Connor |
| 9,536,449 B2 | 1/2017 | Connor |
| 9,640,088 B1 | 5/2017 | Whitehurst et al. |
| 10,102,342 B1 | 10/2018 | Vleugels et al. |
| 10,373,716 B2 | 8/2019 | Vleugels et al. |
| 10,790,054 B1 | 9/2020 | Vleugels et al. |
| 11,069,443 B2 | 7/2021 | Vleugels et al. |
| 11,308,536 B1* | 4/2022 | Adler ............... G06Q 10/083 |
| 2002/0022774 A1 | 2/2002 | Karnieli |
| 2007/0123819 A1 | 5/2007 | Mernoe et al. |
| 2008/0267444 A1 | 10/2008 | Simons-Nikolova et al. |
| 2009/0012433 A1 | 1/2009 | Fernstrom et al. |
| 2010/0160861 A1 | 6/2010 | Causey, III et al. |
| 2010/0188328 A1 | 7/2010 | Dodge et al. |
| 2010/0194573 A1 | 8/2010 | Hoover et al. |
| 2011/0071765 A1* | 3/2011 | Yodfat ............... G16H 20/17 702/19 |
| 2014/0347491 A1 | 11/2014 | Connor |
| 2014/0349256 A1 | 11/2014 | Connor |
| 2015/0217055 A1* | 8/2015 | Booth ............... G16H 20/17 |
| 2015/0379238 A1 | 12/2015 | Connor |
| 2016/0073953 A1 | 3/2016 | Sazonov |
| 2016/0132642 A1 | 5/2016 | Carmi |
| 2016/0283783 A1 | 9/2016 | Yang et al. |
| 2017/0053552 A1* | 2/2017 | Zhong ............... A61B 5/7405 |
| 2018/0174675 A1* | 6/2018 | Roy ............... A61M 5/145 |
| 2020/0135320 A1 | 4/2020 | Meugels |
| 2020/0289373 A1 | 9/2020 | Meugels |
| 2020/0350052 A1* | 11/2020 | Saint ............... G16H 20/30 |
| 2021/0178067 A1 | 6/2021 | Grosman et al. |
| 2021/0178068 A1 | 6/2021 | Miller et al. |
| 2021/0350920 A1 | 11/2021 | Vleugels et al. |

FOREIGN PATENT DOCUMENTS

| | | | |
|---|---|---|---|
| CN | 115039183 A | 9/2022 | |
| EP | 4073813 A1 | 10/2022 | |
| WO | WO-2017132690 A1 * | 8/2017 | ........... A61B 5/0022 |
| WO | 2021119541 A1 | 6/2021 | |

OTHER PUBLICATIONS

Petersen, et al., "A New Software for Initiating and Optimising Insulin Treatment of Out-Patients," Computer Methods and Programs in Biomedicine, 32 (1990), pp. 325-331, Department of Endocrinology, University Hospital of Internal Medicine, Freiburg, F.R.G.

(56) References Cited

OTHER PUBLICATIONS

European Office Action dated Jun. 3, 2022 in Application No. EP17745101.0.
International Search Report and Written Opinion dated Apr. 10, 2017, International Patent Application No. PCT/US2017/015682, filed Jan. 30, 2017, 15 pages.
Ogden, C. L et al., "Prevalence of Childhood and Adult Obesity in the United States, 2011-2012", JAMA, Feb. 26, 2014, vol. 311, No. 8, pp. 806-814.

* cited by examiner

SYNERGISTIC FEATURES AND FUNCTIONS RELATED TO OPERATION OF A MEDICATION DELIVERY SYSTEM AND A MEAL TRANSACTION APPLICATION

CROSS-REFERENCE TO RELATED APPLICATIONS

This application claims the benefit of U.S. provisional patent application Ser. No. 62/935,411, filed Nov. 14, 2019, and U.S. provisional application Ser. No. 62/947,988, filed Dec. 13, 2019.

TECHNICAL FIELD

The present technology is generally related to systems that leverage the output of a meal transaction application. In accordance with certain embodiments, the present technology is related to the control of medical device operation and features based on the output of a meal transaction application.

BACKGROUND

Medical therapy delivery systems, such as fluid infusion devices, are relatively well known in the medical arts, for use in delivering or dispensing an agent, such as insulin or another prescribed medication, to a patient. A typical insulin infusion device includes a fluid pump mechanism and an associated drive system that actuates a plunger or piston of a fluid reservoir to deliver fluid medication from the reservoir to the body of a patient via a fluid delivery conduit between the reservoir and the body of a patient. Use of infusion pump therapy has been increasing, especially for delivering insulin to diabetic patients.

Control schemes have been developed to allow insulin infusion devices to monitor and regulate a patient's blood glucose level in a substantially continuous and autonomous manner. An insulin infusion device can be operated in an automatic mode wherein basal insulin is delivered at a rate that is automatically adjusted for the user. Moreover, an insulin infusion device can be operated to automatically calculate, recommend, and deliver insulin boluses as needed (e.g., to compensate for meals consumed by the user). Ideally, the amount of a meal bolus should be accurately calculated and administered to maintain the user's blood glucose within the desired range. In particular, an automatically generated and delivered meal bolus should safely manage the user's blood glucose level and keep it above a defined threshold level. To this end, an insulin infusion device operating in an automatic mode uses continuous glucose sensor data and control algorithms to regulate the user's blood glucose, based on a target glucose setpoint setting and user-initiated meal announcements that typically include estimations of the amount of carbohydrates to be consumed in an upcoming meal.

BRIEF SUMMARY

The subject matter of this disclosure generally relates to a medical device system and related methodologies that leverage data associated with the use of a meal transaction application (e.g., an application for ordering food delivery).

In one aspect, the present disclosure provides a method that involves: obtaining meal-related data generated by a meal transaction application in response to a meal order for a user; identifying, from the obtained meal-related data, at least one item consumed by or intended to be consumed by the user; retrieving nutritional information for the identified at least one item; and saving a record associated with the user, the record comprising the identified at least one item and the retrieved nutritional information.

In another aspect, the disclosure provides a processor-based system having: computer-readable storage media for program code instructions; and at least one processor. The program code instructions are configurable to cause the at least one processor to perform a method that involves the steps of: obtaining meal-related data generated by a meal transaction application in response to a meal order for a user; identifying, from the obtained meal-related data, at least one item consumed by or intended to be consumed by the user; retrieving nutritional information for the identified at least one item; and saving a record associated with the user, the record comprising the identified at least one item and the retrieved nutritional information.

In another aspect, the disclosure provides a method that involves: obtaining meal-related data generated by a meal transaction application in response to a meal order for a user; identifying, from the obtained meal-related data, at least one item intended to be consumed by the user, and an estimated delivery, pickup, or serving time for the at least one item; retrieving nutritional information for the identified at least one item; determining a dosage of medication for the user, and corresponding timing of the dosage of medication, wherein the determining considers the identified at least one item, the estimated delivery, pickup, or serving time, and the retrieved nutritional information; and generating an output for the determined dosage of medication and the corresponding timing of the dosage.

In yet another aspect, the disclosure provides a processor-based system having: computer-readable storage media comprising program code instructions; and at least one processor. The program code instructions are configurable to cause the at least one processor to perform a method that involves the steps of: obtaining meal-related data generated by a meal transaction application in response to a meal order for a user; identifying, from the obtained meal-related data, at least one item intended to be consumed by the user, and an estimated delivery, pickup, or serving time for the at least one item; retrieving nutritional information for the identified at least one item; determining a dosage of medication for the user, and corresponding timing of the dosage of medication, wherein the determining considers the identified at least one item, the estimated delivery, pickup, or serving time, and the retrieved nutritional information; and generating an output for the determined dosage of medication and the corresponding timing of the dosage.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
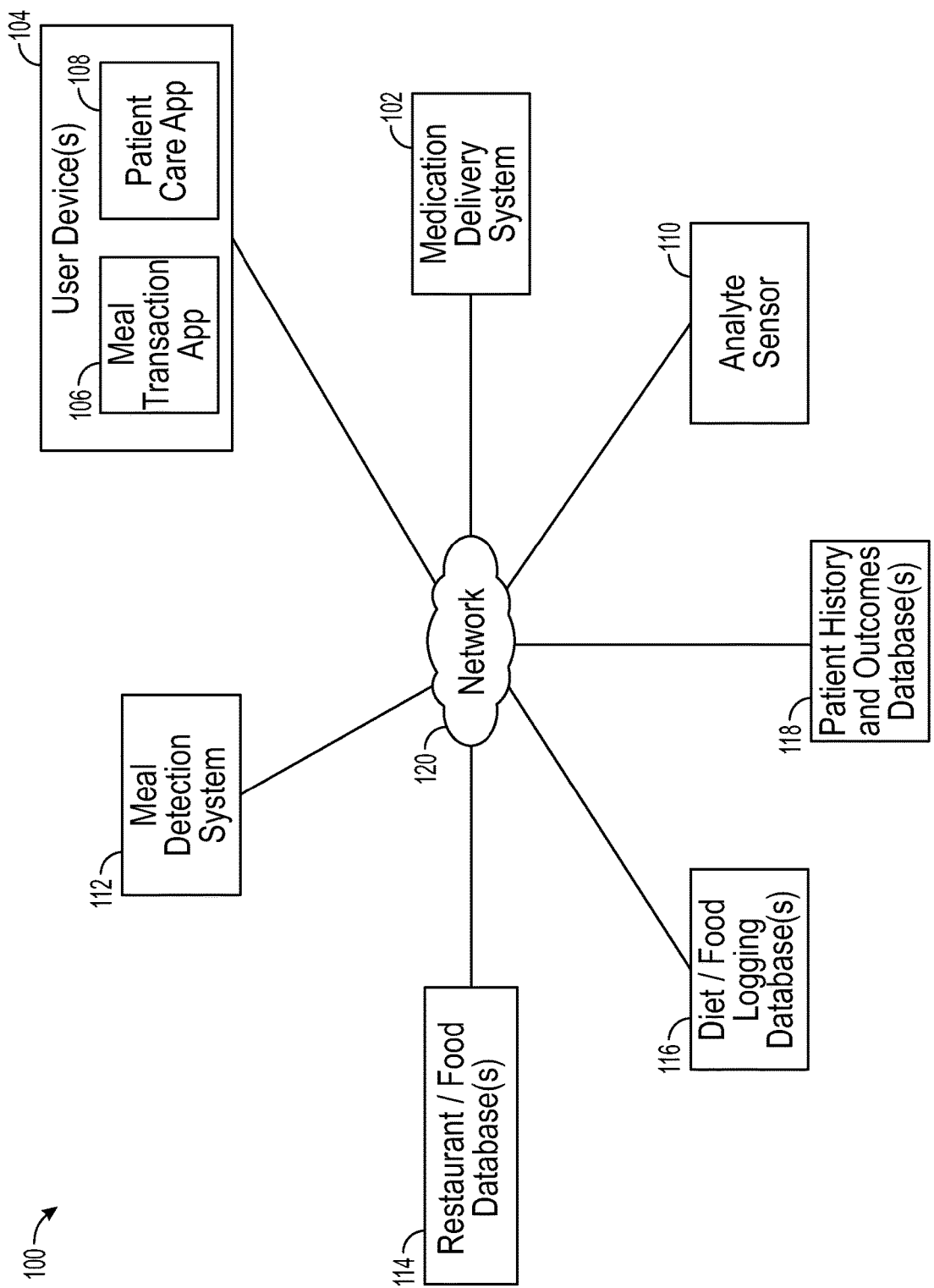
FIG. 1 is a simplified block diagram representation of an exemplary embodiment of a system that includes a medication delivery system informed by data generated by a meal transaction application.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

It should be understood that various aspects disclosed herein may be combined in different arrangements than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be configurable to be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

FIG. 1 is a simplified block diagram representation of an exemplary embodiment of a system 100 that leverages data generated by a meal transaction application (e.g., a food delivery app, a food ordering app, a restaurant website, a telephone meal ordering service, or the like). Certain embodiments of the system 100 include, without limitation: a medication delivery system 102 (or device) that regulates delivery of medication to a user; at least one user device 104 that includes or cooperates with a suitably written and configured meal transaction application 106 and with a suitably written and configured patient care application 108; an analyte sensor 110 to measure a physiological characteristic of the user, such that sensor data obtained from the analyte sensor 110 can be used to control, regulate, or otherwise influence the operation of the medication delivery system 102; a meal detection system 112 that monitors user behavior and/or status to determine whether the user is eating or drinking; at least one restaurant/food database 114; at least one diet/food logging database 116; and at least one patient history and outcomes database 118. Other configurations and topologies for the system 100 are also contemplated here, such as a system that includes additional intermediary, interface, or data repeating devices in the data path between a sending device and a receiving device.

At least some of the components of the system 100 are communicatively coupled with one another to support data communication, signaling, and/or transmission of control commands as needed, via at least one communications network 120. The at least one communications network 120 may support wireless data communication and/or data communication using tangible data communication links. FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the at least one communication network 120.

The system 100 can support any type of medication delivery system 102 that is compatible with the features and functionality described here. For example, the medication delivery system 102 may be realized as a user-activated or user-actuated fluid delivery device, such as a manual syringe, an injection pen, or the like. As another example, the medication delivery system 102 may be implemented as an electronic device that is operated to regulate the delivery of medication fluid to the user. In certain embodiments, however, the medication delivery system 102 includes or is realized as an insulin infusion device, e.g., a portable patient-worn or patient-carried insulin pump. In such embodiments, the analyte sensor 110 includes or is realized as a glucose meter, a glucose sensor, or a continuous glucose monitor. For the sake of brevity, conventional techniques related to insulin infusion device operation, infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Figure 2:
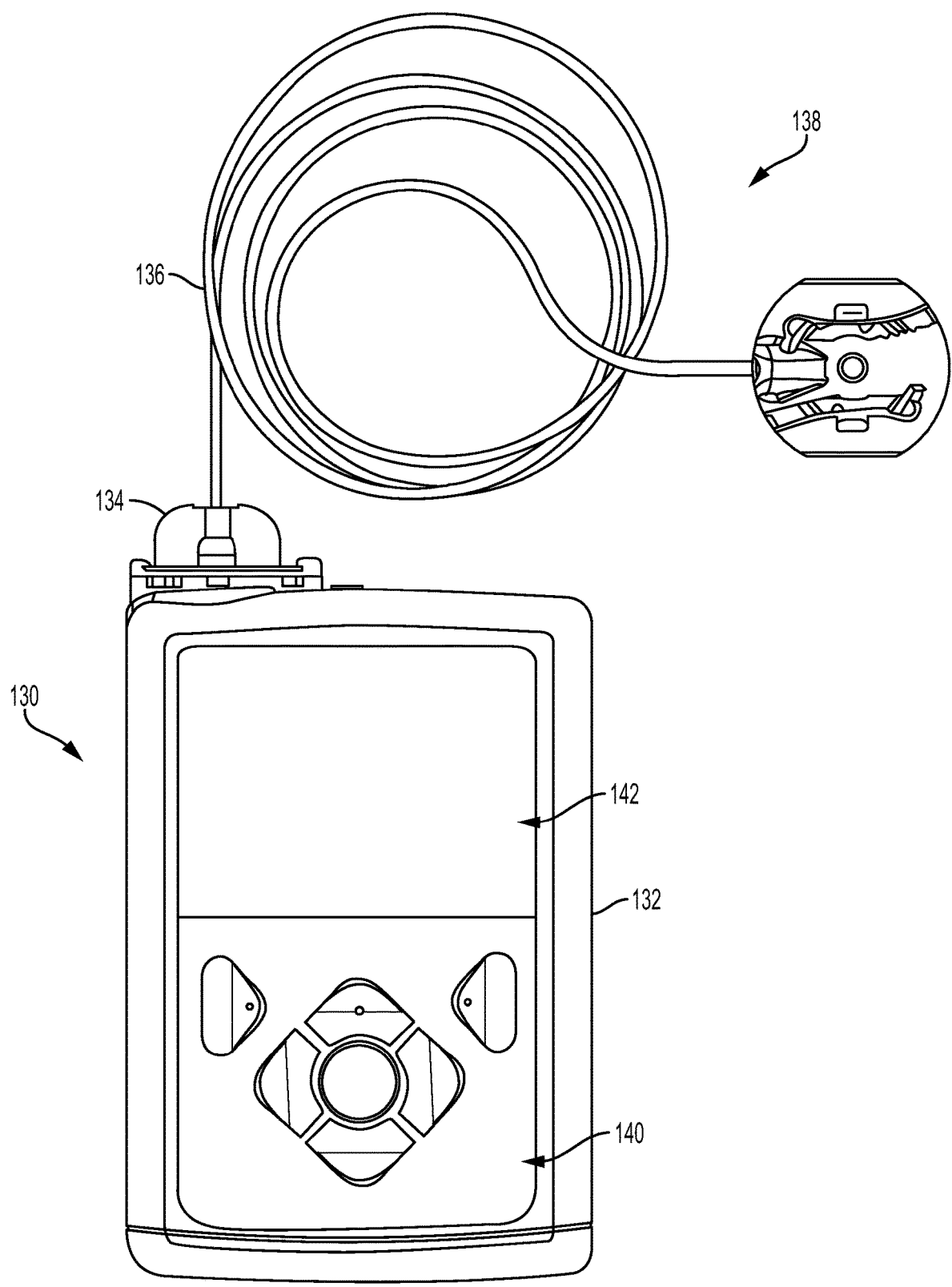
FIG. 2 is a plan view of an exemplary embodiment of an insulin infusion device that is suitable for use as the medication delivery system shown in FIG. 1.

FIG. 2 is a plan view of an exemplary embodiment of an insulin infusion device 130 suitable for use as the medication delivery system 102 shown in FIG. 1. The insulin infusion device 130 is a portable medical device designed to be carried or worn by the patient. The illustrated embodiment of the insulin infusion device 130 includes a housing 132 adapted to receive an insulin-containing reservoir (hidden from view in FIG. 2). An opening in the housing 132 accommodates a fitting 134 (or cap) for the reservoir, with the fitting 134 being configured to mate or otherwise interface with tubing 136 of an infusion set 138 that provides a fluid path to/from the body of the user. In this manner, fluid communication from the interior of the insulin reservoir to the user is established via the tubing 136. The illustrated version of the insulin infusion device 130 includes a human-machine interface (HMI) 140 (or user interface) that includes elements that can be manipulated by the user to administer a bolus of fluid (e.g., insulin), to change therapy settings, to change user preferences, to select display features, and the like. The insulin infusion device 130 also includes a display 142, such as a liquid crystal display (LCD) or another suitable display technology, that can be used to present various types of information or data to the user, such as, without limitation: the current glucose level of the patient; the time; a graph or chart of the patient's glucose level versus time; device status indicators; etc. The insulin infusion device 130 may be configured and controlled to support other features and interactive functions described in more detail below.

Figure 3:
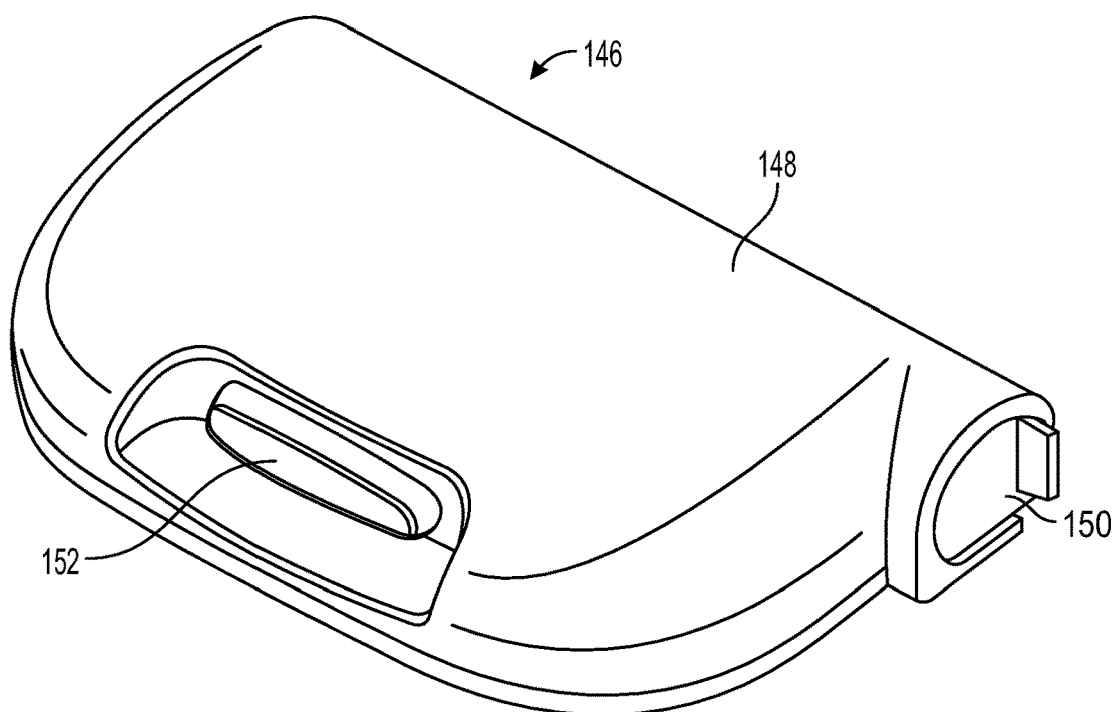
FIG. 3 is a top perspective view of an embodiment of an insulin infusion device implemented as a patch pump device that is suitable for use as the medication delivery system shown in FIG. 1.

FIG. 3 is a top perspective view of an embodiment of an insulin infusion device 146 implemented as a patch pump device that is suitable for use as the medication delivery system 102 shown in FIG. 1. The insulin infusion device 146 can be implemented as a combination device that includes an insertable insulin delivery cannula and an insertable glucose sensor (both of which are hidden from view in FIG. 3). In such an implementation, the glucose sensor may take the place of the separate analyte sensor 110 shown in FIG. 1. The insulin infusion device 146 includes a housing 148 that serves as a shell for a variety of internal components. FIG. 3 shows the insulin infusion device 146 with a removable fluid cartridge module 150 installed and secured therein. The housing 148 is suitably configured to receive, secure, and release the removable fluid cartridge module 150. The fluid infusion device 146 includes at least one user interface feature, which can be actuated by the patient as needed. The illustrated embodiment of the fluid infusion device 146 includes a button 152 that is physically actuated. The button 152 can be a multipurpose user interface if so desired to make it easier for the user to operate the fluid infusion device 146. In this regard, the button 152 can be used in connection with one or more of the following functions, without limitation: waking up the processor and/or electronics of the fluid infusion device 146; triggering an insertion mechanism to insert a fluid delivery cannula and/or an analyte sensor into the subcutaneous space or similar region of the user; configuring one or more settings of the fluid infusion device 146; initiating delivery of medication fluid from the fluid cartridge module 150; initiating a fluid priming operation; disabling alerts or alarms generated by the fluid infusion device 146; and the like. In lieu of the button 152, the fluid infusion device 100 can employ a slider mechanism, a pin, a lever, a switch, a touch-sensitive element, or the like. In certain embodiments, the fluid infusion device 146 may be configured and controlled to support other features and interactive functions described in more detail below.

Figure 4:
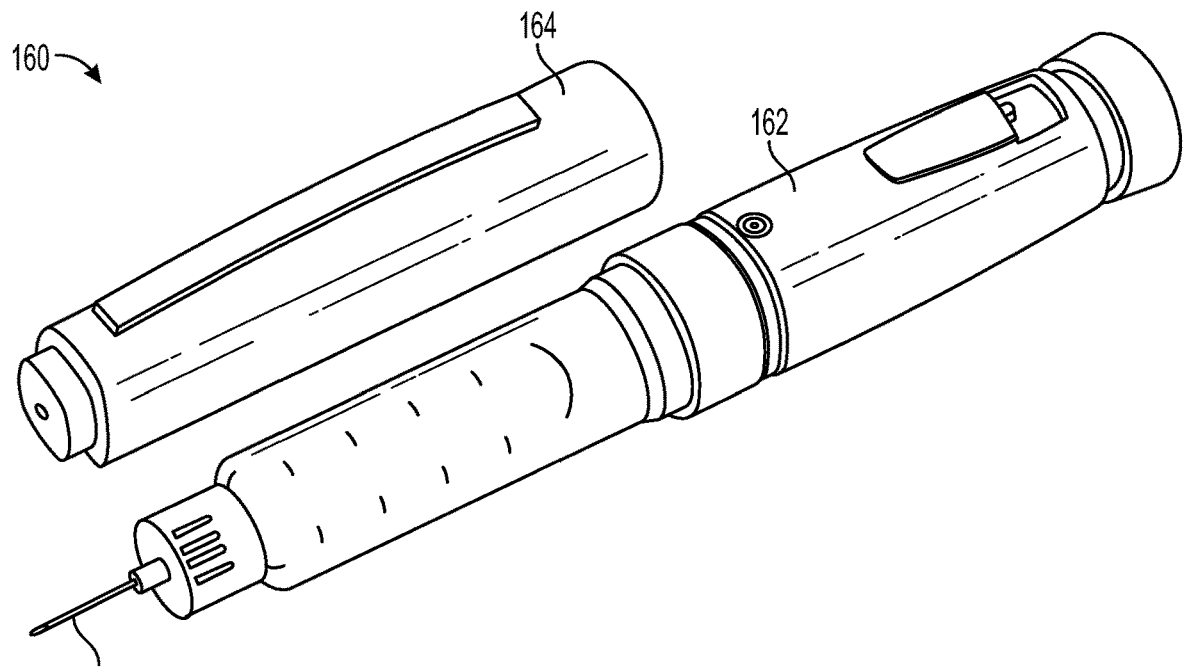
FIG. 4 is a perspective view of an exemplary embodiment of a smart insulin pen that is suitable for use as the medication delivery system shown in FIG. 1.

FIG. 4 is a perspective view of an exemplary embodiment of a smart insulin pen 160 suitable for use as the medication delivery system shown in FIG. 1. The pen 160 includes an injector body 162 and a cap 164. FIG. 4 shows the cap 164 removed from the injector body 162, such that a delivery needle 166 is exposed. The pen 160 includes suitably configured electronics and processing capability to communicate with an application running on a user device, such as a smartphone, to support various functions and features such as: tracking active insulin; calculating insulin dosages (boluses); tracking insulin dosages; monitoring insulin supply levels; patient reminders and notifications; and patient status reporting. In certain embodiments, the smart insulin pen 160 can receive insulin dosage recommendations or instructions and/or recommended dosing times (or a recommended dosing schedule). Moreover, the smart insulin pen 160 may be configured and controlled to support other features and interactive functions described in more detail below.

Figure 5:
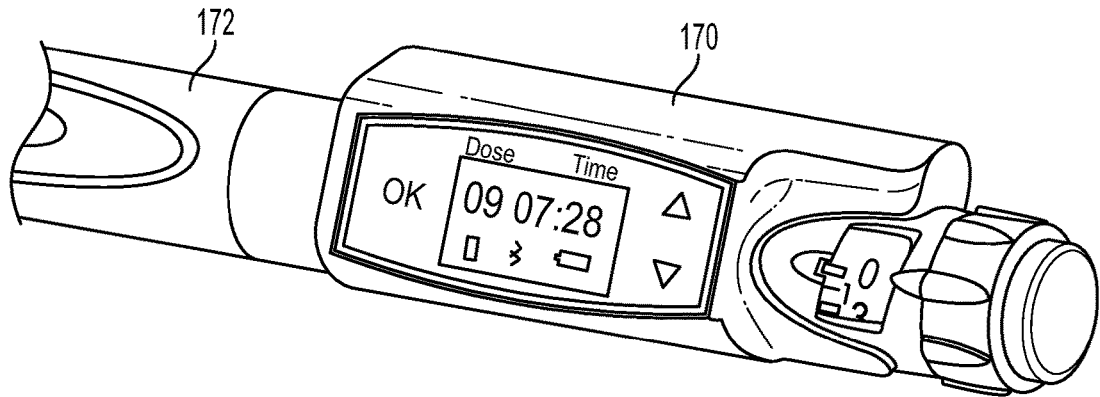
FIG. 5 is a perspective view of an exemplary embodiment of a smart pen accessory that is suitable for use with the medication delivery system shown in FIG. 1.

FIG. 5 is a perspective view of an exemplary embodiment of a smart pen accessory 170 that is suitable for use with the medication delivery system 102 shown in FIG. 1. In particular, the smart pen accessory 170 cooperates with a "non-smart" insulin pen that lacks the intelligence and functionality of a smart insulin pen (as described above). The smart pen accessory 170 can be realized as a pen cap, a clip-on apparatus, a sleeve, or the like. The smart pen accessory 170 is attached to an insulin pen 172 such that the smart pen accessory 170 can measure the amount of insulin delivered by the insulin pen 172. The insulin dosage data is stored by the smart pen accessory 170 along with corresponding date/time stamp information. In certain embodiments, the smart pen accessory 170 can receive, store, and process additional patient-related or therapy-related data, such as glucose data. Indeed, the smart pen accessory 170 may also support various features and functions described above in the context of the smart insulin pen 160. For example, the smart pen accessory 170 may be configured to receive insulin dosage recommendations or instructions and/or recommended dosing times (or a recommended dosing schedule). Moreover, the smart pen accessory 170 may be configured and controlled to support other features and interactive functions described in more detail below.

Generally, a fluid infusion device (such as an insulin infusion device) includes a fluid pump mechanism having a motor or other actuation arrangement that is operable to linearly displace a plunger (or stopper) of a fluid reservoir provided within the fluid infusion device to deliver a dosage of fluid medication, such as insulin, to the body of a user. Dosage commands that govern operation of the motor may be generated in an automated manner in accordance with the delivery control scheme associated with a particular operating mode, and the dosage commands may be generated in a manner that is influenced by a current (or most recent) measurement of a physiological condition in the body of the user. For a glucose control system suitable for use by diabetic patients, a closed-loop or automatic operating mode can be used to generate insulin dosage commands based on a difference between a current (or most recent) measurement of the interstitial fluid glucose level in the body of the user and a target (or reference) glucose setpoint value. In this regard, the rate of infusion may vary as the difference between a current measurement value and the target measurement value fluctuates. For purposes of explanation, the subject matter is described herein in the context of the infused fluid being insulin for regulating a glucose level of a user (or patient); however, it should be appreciated that many other fluids may be administered through infusion, and the subject matter described herein is not necessarily limited to use with insulin.

The analyte sensor 110 may communicate sensor data to the medication delivery system 102 for use in regulating or controlling operation of the medication delivery system 102. Alternatively or additionally, the analyte sensor 110 may communicate sensor data to one or more other components in the system 100, such as a user device 104, for use with the patient care application 108.

The system 100 can support any number of user devices 104 linked to the particular user or patient. In this regard, a user device 104 may be, without limitation: a smartphone device; a laptop, desktop, or tablet computer device; a medical device; a wearable device; a global positioning system (GPS) receiver device; a system, component, or feature onboard a vehicle; a smartwatch device; a television system; a household appliance; a video game device; a media player device; or the like. Any given user device 104 can host, run, or otherwise execute the meal transaction application 106 and/or the patient care application 108. In certain embodiments, for example, the user device 104 is implemented as a smartphone with the meal transaction application 106 and the patient care application 108 installed thereon. In accordance with another example, the meal transaction application 106 is implemented in the form of a website or webpage, e.g., a website of a restaurant that supports online ordering. In accordance with another example, the medication delivery system 102 executes the patient care application 108 as a native function. In accordance with another example, the medication delivery system 102 executes the meal transaction application 106 as a native function.

For the example described here, the medication delivery system 102 and the at least one user device 104 are owned by, operated by, or otherwise linked to a user/patient. In certain embodiments, at least some of the features or output of the meal transaction application 106 can be used to influence features, functions, and/or therapy-related operations of the medication delivery system 102. In certain embodiments, at least some of the features or output of the meal transaction application 106 can be used in connection with food logging, diet tracking, or journal activity of the user.

As described in more detail below, the meal detection system 112 includes one or more sensors, detectors, measurement devices, and/or readers to automatically determine whether the user is eating or drinking. The meal detection system 112 may communicate user status data (that indicates eating/drinking status of the user) directly to the medication delivery system 102, which receives and processes the user status data in an appropriate manner for use in regulating or controlling certain functions of the medication delivery system 102. Alternatively or additionally, the meal detection system 112 may communicate user status data to a user device 104, such that the user device 104 can process the user status data and inform the user or the medication delivery system 102 as needed (e.g., remotely regulate or control certain functions of the medication delivery system 102). Alternatively or additionally, the meal detection system 112 may communicate user status data to one or more cloud computing systems or servers for appropriate processing and handling in the manner described herein.

In certain embodiments, the meal detection system 112 and the medication delivery system 102 are implemented as physically distinct and separate components, as depicted in FIG. 1. In such embodiments, the meal detection system 112 is external to the medication delivery system 102 and is realized as an ancillary component, relative to the medication delivery system 102. In accordance with alternative embodiments, however, the medication delivery system 102 and the meal detection system 112 can be combined into a single hardware component or provided as a set of attached hardware devices. For example, the medication delivery system 102 may include the meal detection system 112 or integrate the functionality of the meal detection system 112. Similarly, the analyte sensor 110 can be incorporated with the medication delivery system 102 or the meal detection system 112. These and other arrangements, deployments, and topologies of the system 100 are contemplated by this disclosure.

The meal transaction application 106 enables the user to order meals (e.g., food, drinks, snacks or any number of consumable items) from a restaurant, grocery store, market, or any suitable vendor. A meal order handled by the meal transaction application 106 may include consumable items for one or more people, including the user/patient. Accordingly, the meal transaction application 106 or the patient care application 108 may be configured to allow the user (or another person) to indicate which ordered items are to be consumed by the user. The system 100 may include or support a plurality of different meal transaction applications 106, which may be published by different restaurants, grocery stores, food/drink vendors or distributors, markets, delivery services, caregiver organizations, or the like. For example, any or all of the following popular applications may serve as a meal transaction application 106 in the system 100: GRUBHUB™; DOORDASH™; UBEREATS™; POSTMATES™; INSTACART™; CHOWNOW™. Moreover, a restaurant may have a suitable meal transaction application 106 on its website to enable customers to place online orders for delivery or pickup, or to place advance dine-in orders.

The meal transaction application 106 supports itemized ordering that identifies specific food/drink items to be consumed by the user. At least some of the items contained in a meal order (ideally, all of the items) have corresponding entries in the at least one restaurant/food database 114, which contains nutritional information related to those items. A restaurant/food database 114 may reside at a user device 104, at the medication delivery system 102, at the meal detection system 112, or at any network-accessible location (e.g., a cloud-based database or server system). In certain embodiments, a restaurant/food database 114 may be included with a meal transaction application 106, a patient care application 108, or both. The at least one restaurant/food database 114 enables the system 100 to intelligently and accurately respond, in view of specific items that have been or will be consumed by the user, as described in more detail below.

A meal order that identifies specific food/drink items to be consumed by the user can be leveraged to create, update, or maintain a log, journal, or diary for the user (e.g., a nutrition, diet, food, or calorie counting log). To this end, the nutritional information related to ordered items can be saved in an appropriate record, database object, or log that is linked to the user. Accordingly a diet/food logging database 116 may reside at a user device 104, at the medication delivery system 102, at the meal detection system 112, or at any network-accessible location (e.g., a cloud-based database or server system). In certain embodiments, a diet/food logging database 116 may be included with a meal transaction application 106, a patient care application 108, or both. The at least one diet/food logging database 116 enables the system 100 to accurately keep track of a user's food and drink intake based on meal orders handled by a meal transaction application 106.

The at least one patient history and outcomes database 118 includes historical data related to the user's physiological responses to food and drink consumption. More specifically, the database 118 maintains historical data corresponding to specific food/drink items that can be ordered via the meal transaction application 106, along with physiological outcome data that indicates how the user reacted to those specific food/drink items. This information can be used to provide valuable feedback while the user is placing a meal order via the meal transaction application 106. Assume, for example, that the user has selected "Combo Meal #8" with the meal transaction application. The patient care application 108 may consult the patient history and outcomes database 118, search for historical outcomes that result from eating the Combo Meal #8, and generate an applicable insight message or a notification to the user. Such a message may read, for example: "Your glucose went above your target the last few times you had Combo Meal #8. Consider a smaller portion or a different meal."

A patient history and outcomes database 118 may reside at a user device 104, at the medication delivery system 102, at the meal detection system 112, or at any network-accessible location (e.g., a cloud-based database or server system). In certain embodiments, a patient history and outcomes database 118 may be included with a meal transaction application 106, a patient care application 108, or both. The patient history and outcomes database 118 enables the system 100 to generate recommendations, warnings, and guidance for the user before a meal order is completed.

For clarity and ease of description, FIG. 1 depicts the databases 114, 116, 118 as distinct blocks. In certain embodiments, however, any number of the databases 114, 116, 118 can be integrated or implemented together with one database management system. In this regard, one or more computer-based hardware systems or components can be utilized to implement the databases 114, 116, 118, as appropriate for the particular embodiment.

Figure 6:
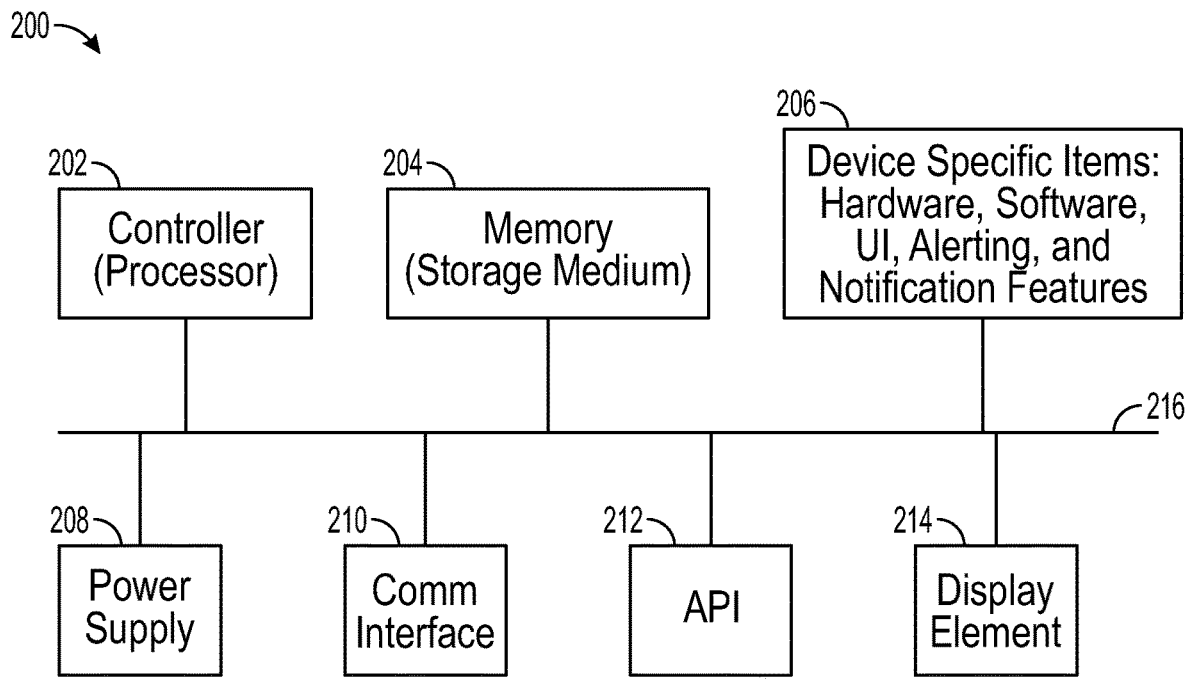
FIG. 6 is a block diagram representation of an exemplary embodiment of a computer-based or processor-based device suitable for deployment in the system shown in FIG. 1.

In accordance with certain embodiments, any or all of the components shown in FIG. 1 can be implemented as a computer-based or a processor-based device, system, or component having suitably configured hardware and software written to perform the functions and methods needed to support the features described herein. In this regard, FIG. 6 is a simplified block diagram representation of an exemplary embodiment of a computer-based or processor-based device 200 that is suitable for deployment in the system 100 shown in FIG. 1.

The illustrated embodiment of the device 200 is intended to be a high-level and generic representation of one suitable platform. In this regard, any computer-based or processor-based component of the system 100 can utilize the architecture of the device 200. The illustrated embodiment of the device 200 generally includes, without limitation: at least one controller (or processor) 202; a suitable amount of memory 204 that is associated with the at least one controller 202; device-specific items 206 (including, without limitation: hardware, software, firmware, user interface (UI), alerting, and notification features); a power supply 208 such as a disposable or rechargeable battery; a communication interface 210; at least one application programming interface (API) 212; and a display element 214. Of course, an implementation of the device 200 may include additional elements, components, modules, and functionality configured to support various features that are unrelated to the primary subject matter described here. For example, the device 200 may include certain features and elements to support conventional functions that might be related to the particular implementation and deployment of the device 200. In practice, the elements of the device 200 may be coupled together via at least one bus or any suitable interconnection architecture 216.

The at least one controller 202 may be implemented or performed with a general purpose processor, a content addressable memory, a microcontroller unit, a digital signal processor, an application specific integrated circuit, a field programmable gate array, any suitable programmable logic device, discrete gate or transistor logic, discrete hardware components, or any combination designed to perform the functions described here. Moreover, the at least one controller 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as at least one memory element, device, module, or unit, such as: RAM memory, flash memory, EPROM memory, EEPROM memory, registers, a hard disk, a removable disk, a CD-ROM, or any other form of storage medium known in the art. In this regard, the memory 204 can be coupled to the at least one controller 202 such that the at least one controller 202 can read information from, and write information to, the memory 204. In the alternative, the memory 204 may be integral to the at least one controller 202. As an example, the at least one controller 202 and the memory 204 may reside in an ASIC. At least a portion of the memory 204 can be realized as a computer storage medium that is operatively associated with the at least one controller 202, e.g., a tangible, non-transitory computer-readable medium having computer-executable instructions stored thereon. The computer-executable instructions are configurable to be executed by the at least one controller 202 to cause the at least one controller 202 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific items 206 may vary from one embodiment of the device 200 to another. For example, the device-specific items 206 will support: sensor device operations when the device 200 is realized as a sensor device; smartphone features and functionality when the device 200 is realized as a smartphone; activity tracker features and functionality when the device 200 is realized as an activity tracker; smart watch features and functionality when the device 200 is realized as a smart watch; medical device features and functionality when the device is realized as a medical device; etc. In practice, certain portions or aspects of the device-specific items 206 may be implemented in one or more of the other blocks depicted in FIG. 6.

If present, the UI of the device 200 may include or cooperate with various features to allow a user to interact with the device 200. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The UI may include one or more graphical user interface (GUI) control elements that enable a user to manipulate or otherwise interact with an application via the display element 214. The display element 214 and/or the device-specific items 206 may be utilized to generate, present, render, output, and/or annunciate alerts, alarms, messages, or notifications that are associated with operation of the medication delivery system 102, associated with a status or condition of the user, associated with operation, status, or condition of the system 100, etc.

The communication interface 210 facilitates data communication between the device 200 and other components as needed during the operation of the device 200. In the context of this description, the communication interface 210 can be employed to transmit or stream device-related control data, patient-related user status (e.g., meal detection or status data), device-related status or operational data, sensor data, calibration data, and the like. It should be appreciated that the particular configuration and functionality of the communication interface 210 can vary depending on the hardware platform and specific implementation of the device 200. In practice, an embodiment of the device 200 may support wireless data communication and/or wired data communication, using various data communication protocols. For example, the communication interface 210 could support one or more wireless data communication protocols, techniques, or methodologies, including, without limitation: RF; IrDA (infrared); Bluetooth; BLE; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication interface 210 could support one or more wired/cabled data communication protocols, including, without limitation: Ethernet; powerline; home network communication protocols; USB; IEEE 1394 (Firewire); hospital network communication protocols; and proprietary data communication protocols.

The at least one API 212 supports communication and interactions between software applications and logical components that are associated with operation of the device 200. For example, one or more APIs 212 may be configured to facilitate compatible communication and cooperation between the meal transaction application 106 and the patient care application 108, and to facilitate receipt and processing of data from sources external to the device 200 (e.g., databases or remote devices and systems).

The display element 214 is suitably configured to enable the device 200 to render and display various screens, recommendation messages, alerts, alarms, notifications, GUIs, GUI control elements, drop down menus, auto-fill fields, text entry fields, message fields, or the like. Of course, the display element 214 may also be utilized for the display of other information during the operation of the device 200, as is well understood. Notably, the specific configuration, operating characteristics, size, resolution, and functionality of the display element 214 can vary depending upon the implementation of the device 200.

Figure 7:
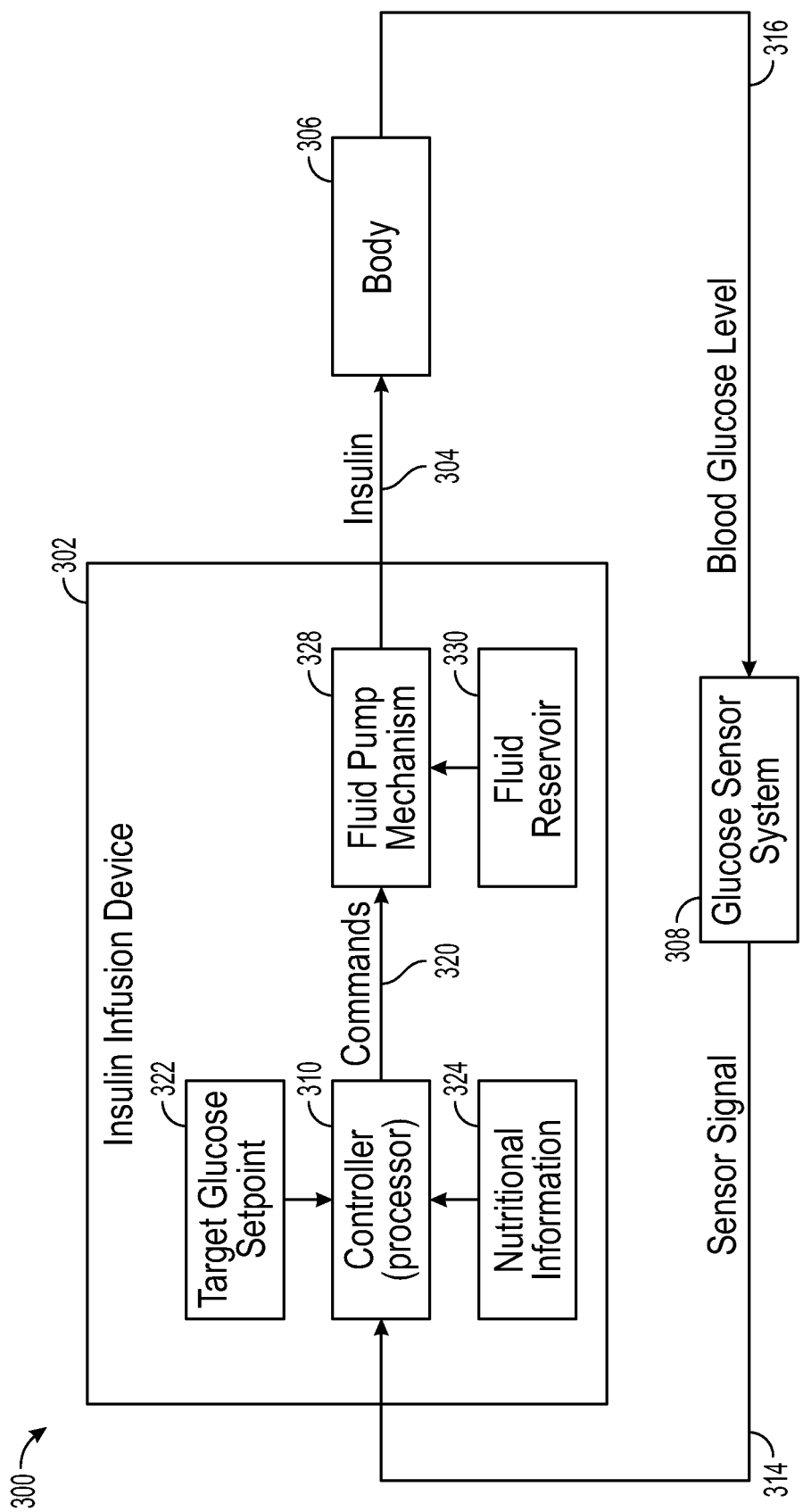
FIG. 7 is a block diagram representation of a closed loop glucose control system arranged in accordance with certain embodiments.

As mentioned above, the medication delivery system 102 is suitably configured and programmed to support an automatic mode to automatically control delivery of insulin to the user. In this regard, FIG. 7 is a simplified block diagram representation of a closed loop glucose control system 300 arranged in accordance with certain embodiments. The system 300 depicted in FIG. 7 functions to regulate the rate of fluid infusion into a body of a user based on feedback from an analyte concentration measurement taken from the body. In particular embodiments, the system 300 is implemented as an automated control system for regulating the rate of insulin infusion into the body of a user based on a glucose concentration measurement taken from the body. The system 300 is designed to model the physiological response of the user to control an insulin infusion device 302 in an appropriate manner to release insulin 304 into the body 306 of the user in a similar concentration profile as would be created by fully functioning human (3-cells when responding to changes in blood glucose concentrations in the body. Thus, the system 300 simulates the body's natural insulin response to blood glucose levels and not only makes efficient use of insulin, but also accounts for other bodily functions as well since insulin has both metabolic and mitogenic effects.

Certain embodiments of the system 300 include, without limitation: the insulin infusion device 302; a glucose sensor system 308 (e.g., the analyte sensor 110 shown in FIG. 1); and at least one controller 310, which may be incorporated in the insulin infusion device 302 as shown in FIG. 7. The glucose sensor system 308 generates a sensor signal 314 representative of blood glucose levels 316 in the body 306, and provides the sensor signal 314 to the at least one controller 310. The at least one controller 310 receives the sensor signal 314 and generates commands 320 that regulate the timing and dosage of insulin 304 delivered by the insulin infusion device 302. The commands 320 are generated in response to various factors, variables, settings, and control algorithms utilized by the insulin infusion device 302. For example, the commands 320 (and, therefore, the delivery of insulin 304) can be influenced by a target glucose setpoint value 322 that is maintained and regulated by the insulin infusion device 302. Moreover, the commands 320 (and, therefore, the delivery of insulin 304) can be influenced by nutritional information 324 obtained for specific items of food/drink that have been consumed or will be consumed by the user.

Generally, the glucose sensor system 308 includes a continuous glucose sensor, sensor electrical components to provide power to the sensor and generate the sensor signal 314, a sensor communication system to carry the sensor signal 314 to the at least one controller 310, and a sensor system housing for the electrical components and the sensor communication system. As mentioned above with reference to FIG. 6, the glucose sensor system 308 may be implemented as a computer-based or processor-based component having the described configuration and features.

Typically, the at least one controller 310 includes controller electrical components and software to generate commands for the insulin infusion device 302 based on the sensor signal 314, the target glucose setpoint value 322, the nutritional information 324, and other user-specific parameters, settings, and factors. The at least one controller 310 may include a controller communication system to receive the sensor signal 314 and issue the commands 320.

Generally, the insulin infusion device 302 includes a fluid pump mechanism 328, a fluid reservoir 330 for the medication (e.g., insulin), and an infusion tube to infuse the insulin 304 into the body 306. In certain embodiments, the insulin infusion device 302 includes an infusion communication system to handle the commands 320 from the at least one controller 310, electrical components and programmed logic to activate the fluid pump mechanism 328 motor according to the commands 320, and a housing to hold the components of the insulin infusion device 302. Accordingly, the fluid pump mechanism 328 receives the commands 320 and delivers the insulin 304 from the fluid reservoir 330 to the body 306 in accordance with the commands 320. It should be appreciated that an embodiment of the insulin infusion device 302 can include additional elements, components, and features that may provide conventional functionality that need not be described herein. Moreover, an embodiment of the insulin infusion device 302 can include alternative elements, components, and features if so desired, as long as the intended and described functionality remains in place. In this regard, as mentioned above with reference to FIG. 6, the insulin infusion device 302 may be implemented as a computer-based or processor-based components having the described configuration and features, including the display element 214 or other device-specific items 206 as described above.

The at least one controller 310 is configured and programmed to regulate the operation of the fluid pump mechanism 328 and other functions of the insulin infusion device 302. The at least one controller 310 controls the fluid pump mechanism 328 to deliver the fluid medication (e.g., insulin) from the fluid reservoir 330 to the body 306. As mentioned above, the at least one controller 310 can be housed in the infusion device housing, wherein the infusion communication system is an electrical trace or a wire that carries the commands 320 from the at least one controller 310 to the fluid pump mechanism 328. In alternative embodiments, the at least one controller 310 can be housed in the sensor system housing, wherein the sensor communication system is an electrical trace or a wire that carries the sensor signal 314 from the sensor electrical components to the at least one controller 310. In accordance with some embodiments, the at least one controller 310 has its own housing or is included in a supplemental or ancillary device. In other embodiments, the at least one controller 310, the insulin infusion device 302, and the glucose sensor system 308 are all located within one common housing.

The meal detection system 112 employs at least one sensor to obtain corresponding user-specific sensor data (i.e., user status data). The obtained user status data is processed or analyzed by the meal detection system 112 and/or by a suitably configured device or component of the system 100 to determine whether the user is eating, drinking, or otherwise consuming an edible or consumable item (or items). The obtained user status data may also be processed or analyzed to obtain certain meal-related parameters, characteristics, and/or metadata for the user. For example, the obtained user status data may identify, include, or indicate any or all of the following, without limitation: timestamp data corresponding to when the user starts eating or drinking; timestamp data corresponding to when the user stops eating or drinking; timestamp data corresponding to individual bites, sips, or other body motions or gestures that are indicative of eating or drinking; location data; one or more physiological characteristics of the user; user posture or position information, which indicates orientation of the user's body during mealtime; body temperature; heartrate; blood pressure; respiratory rate; sweat level; images or video of the user; etc.

The meal detection system 112 may include, cooperate with, or be implemented as a gesture-based physical behavior detection system, a motion-based physical behavior detection system, an activity-based physical behavior detection system, a heartrate-based activity detection system, or the like. In certain embodiments, the meal detection system 112 may be realized as a unitary "self-contained" wearable system that communicates with one or more other components of the system 100. For example, the meal detection system 112 can be implemented with at least one wearable device such as an activity monitor device, a smart watch device, a smart bracelet or wristband device, or the like. In some embodiments, the meal detection system 112 may be realized as at least one portable or wearable device that includes or communicates with one or more external or ancillary sensor devices, units, or components. For example, the meal detection system 112 can be implemented with a wearable or portable smart device that is linked with one or more external sensors worn or carried by the user. These and other possible deployments of the meal detection system 112 are contemplated by this disclosure. In this regard, United States patent publication number US 2020/0135320 and United States patent publication number US 2020/0289373 disclose gesture-based physical behavior detection systems that are suitable for use as the meal detection system 112; the entire content of these United States patent documents is incorporated by reference herein.

Figure 8:
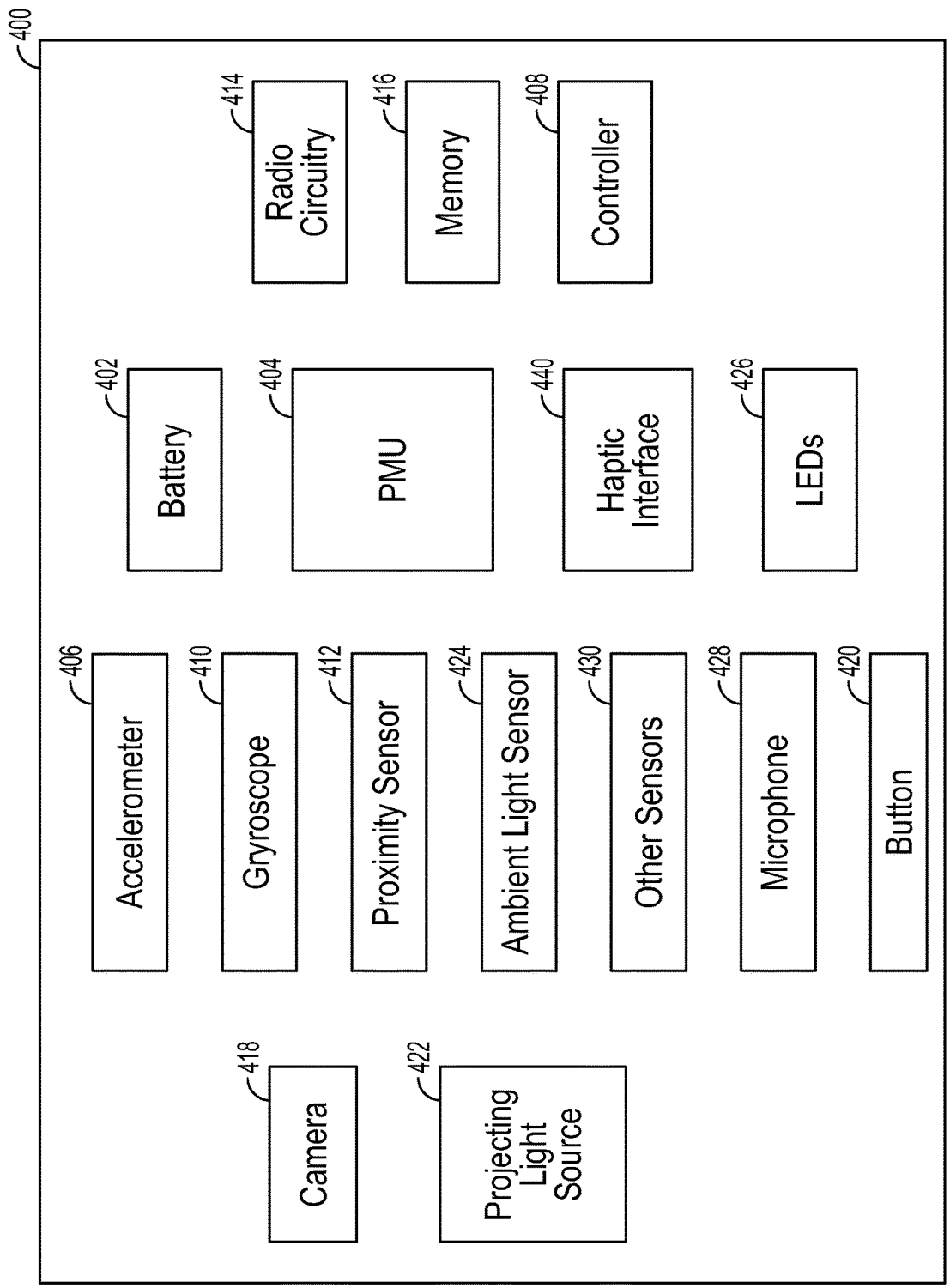
FIG. 8 is a block diagram representation of a meal detection system arranged in accordance with certain embodiments.

FIG. 8 is a block diagram representation of a meal detection system 400 arranged in accordance with certain embodiments. The meal detection system 400 is suitable for use with the system 100 shown FIG. 1. In certain embodiments, the meal detection system 400 is deployed as a wearable electronic device in the form factor of a bracelet or wristband that is worn around the wrist or arm of a user's dominant hand. The meal detection system 400 may optionally be implemented using a modular design, wherein individual modules include one or more subsets of the disclosed components and overall functionality. The user may choose to add specific modules based on personal preferences and requirements.

The meal detection system 400 includes a battery 402 and a power management unit (PMU) 404 to deliver power at the proper supply voltage levels to all electronic circuits and components. The PMU 404 may also include battery-recharging circuitry. The PMU 404 may also include hardware, such as switches, that allows power to specific electronics circuits and components to be cut off when not in use.

When there is no movement-based or gesture-based behavior event in progress, most circuitry and components in the meal detection system 400 are switched off to conserve power. Only circuitry and components that are required to detect or help predict the start of a behavior event of interest (such as sleeping or waking) may remain enabled. For example, if no motion is being detected, all sensor circuits but an accelerometer 406 may be switched off and the accelerometer 406 may be put in a low-power wake-on-motion mode or in another lower power mode that consumes less power and uses less processing resources than its high performance active mode. A controller 408 of the meal detection system 400 may also be placed into a low-power mode to conserve power. When motion or a certain motion pattern is detected, the accelerometer 406 and/or the controller 408 may switch into a higher power mode and additional sensors such as, for example, a gyroscope 410 and/or a proximity sensor 412 may also be enabled. When a potential start of a movement-based or gesture-based event is detected, memory variables for storing event-specific parameters, such as gesture types, gesture duration, etc. can be initialized.

In another example, upon detection of user motion, the accelerometer 406 switches into a higher power mode, but other sensors remain switched off until the data from the accelerometer 406 indicates that the start of a behavior event has likely occurred. At that point in time, additional sensors such as the gyroscope 410 and the proximity sensor 412 may be enabled.

In another example, when there is no behavior event in progress, both the accelerometer 406 and gyroscope 410 are enabled but at least one of either the accelerometer 406 or the gyroscope 410 is placed in a lower power mode compared to their regular power mode. For example, the sampling rate may be reduced to conserve power. Similarly, the circuitry required to transfer data from the meal detection system 400 to a destination device may be placed in a lower power mode. For example, radio circuitry 414 could be disabled. Similarly, the circuitry required to transfer data from the meal detection system 400 may be placed in a lower power mode. For example, the radio circuitry 414 could be disabled until a possible or likely start of a behavior event has been determined. Alternatively, it may remain enabled but in a low power state to maintain the connection between the meal detection system 400 and one or more other components of the system 100, but without transferring user status data, sensor data, or the like.

In yet another example, all motion-detection related circuitry may be switched off if, based on certain metadata, it is determined that the occurrence of a particular behavior event, such as a food intake event, is unlikely. This may be desirable to further conserve power. Metadata used to make this determination may, among other things, include one or more of the following: time of the day, location, ambient light levels, proximity sensing, and detection that the meal detection system 400 has been removed from the wrist or hand, detection that the meal detection system 400 is being charged, or the like. Metadata may be generated and collected by the meal detection system 400. Alternatively, metadata may be collected by another device that is external to the meal detection system 400 and is configured to directly or indirectly exchange information with the meal detection system 400. It is also possible that some metadata is generated and collected by the meal detection system 400, while other metadata is generated and collected by a device that is external to the meal detection system 400. In case some or all of the metadata is generated and collected external to the meal detection system 400, the meal detection system 400 may periodically or from time to time power up its radio circuitry 414 to retrieve metadata related information from another device.

In certain embodiments, some or all of the sensors may be turned on or placed in a higher power mode if certain metadata indicates that the occurrence of a particular behavior event, such as the user beginning to eat, is likely. Metadata used to make this determination may, among other things, include one or more of the following: time of the day; location; ambient light levels; proximity sensing; historical user behavior patterns. Some or all of the metadata may be collected by the meal detection system 400 or by an ancillary device that cooperates or communicates with the meal detection system 400, as mentioned above.

User status data used to track certain aspects of a user's behavior may be stored locally inside memory 416 of the meal detection system 400 and processed locally using the controller 408 of the meal detection system 400. User status data may also be transferred to the medication delivery system 102, the meal transaction application 106, the patient care application 108, and/or one or more of the databases 114, 116, 118 mentioned above with reference to FIG. 1 (such that the user status data can be processed, analyzed, or otherwise utilized by the applications or components that receive the user status data). It is also possible that some of the processing and analysis are performed locally by the meal detection system 400, while further processing and analysis are performed by one or more other components of the system 100.

The detection of the start of a behavior event, such as the start of a meal, may trigger the power up and/or activation of additional sensors and circuitry, such as a camera 418. Power up and/or activation of additional sensors and circuitry may occur at the same time as the detection of the behavior event of interest or some time thereafter. Specific sensors and circuitry may be turned on only at specific times during a detected event, and may be switched off otherwise to conserve power. It is also possible that the camera 418 only gets powered up or activated upon explicit user intervention such as, for example, pushing and holding a button 420. Releasing the button 420 may turn off the camera 418 to conserve power.

When the camera 418 is powered up, a projecting light source 422 may also be enabled to provide visual feedback to the user about the area that is within view of the camera or to otherwise illuminate the field of view. Alternatively, the projecting light source 422 may only be activated sometime after the camera 418 has been activated. In certain cases, additional conditions may need to be met before the projecting light source 422 is activated. Such conditions may include: the determination that the projecting light source 422 is likely aiming in the direction of the object of interest; the determination that the meal detection system 400 is not moving excessively; or the like. In some embodiments, one or more light emitting diodes (LEDs) 426 may be used as the projecting light source 422.

Images may be tagged with additional information or metadata such as: camera focal information; proximity information from the proximity sensor 412; ambient light levels information from an ambient light sensor 424; timestamp information; etc. Such additional information or metadata may be used during the processing and analysis of the user status data.

The projecting light source 422 may also be used to communicate other information. As an example, an ancillary device may use inputs from one or more proximity sensors 412, process those inputs to determine if the camera 418 is within the proper distance range from the object of interest, and use one or more light sources to communicate that the camera is within the proper distance range, that the user needs to increase the distance between camera and the object of interest, or that the user needs to reduce the distance between the camera and the object of interest.

The projecting light source 422 may also be used in combination with the ambient light sensor 424 to communicate to the user if the ambient light is insufficient or too strong for an adequate quality image capture. The projecting light source 422 may also be used to communicate information including, but not limited to, a low battery situation or a functional defect.

The projecting light source 422 may also be used to communicate dietary coaching information. As an example, the projecting light source 422 might, among other things, indicate if not enough or too much time has expired since a previous food intake event, or may communicate to the user how he/she is doing against specific dietary goals.

Signaling mechanisms to convey specific messages using one or more projecting light sources 422 may include, but are not limited to, one or more of the following: specific light intensities or light intensity patterns; specific light colors or light color patterns; specific spatial or temporal light patterns. Multiple mechanisms may also be combined to signal one specific message.

A microphone 428 may be used by the user to add specific or custom labels or messages to a detected event and/or image. In certain embodiments, audio captured by the microphone 428 can be processed to assist in the determination of whether the user is eating or drinking. Audio snippets may be processed by a voice recognition engine.

In certain embodiments, the accelerometer 406 (possibly combined with other sensors, including other inertial sensors) may, in addition to tracking at least one parameter that is directly related to a gesture-based behavior event, also be used to track one or more parameters that are not directly related to that particular event. Such parameters may, among other things, include physical activity, sleep, stress, or illness.

In addition to the particular sensors, detectors, and components mentioned above, the meal detection system 400 may include or cooperate with any number of other sensors 430 as appropriate for the particular embodiment. For example, and without limitation, the meal detection system 400 may include or cooperate with any or all of the following: a heartrate monitor; a physiological characteristic or analyte sensor; a continuous glucose monitor; a GPS receiver; and any other sensor, monitor, or detector mentioned elsewhere herein. The meal detection system 400 obtains user status data from one or more of its sensors, detectors, and sources, wherein the user status data indicates meal consumption status of the user. The user status data can be analyzed and processed by the meal detection system 400 (and/or by one or more other components of the system 100) to determine whether the user is eating or drinking and, in certain embodiments, to determine additional information, characteristics, or metrics related to the user's eating/drinking status. In certain embodiments, the meal detection system 400 and/or an ancillary system or device determines the user's meal activity status primarily based on the output of user-worn motion sensors, movement sensors, one or more inertial sensors (e.g., one or more accelerometers and/or one or more gyroscopes), one or more GPS sensors, one or more magnetometers, one or more force or physical pressure sensors, or the like, which are suitably configured, positioned, and arranged to measure physical movement or motion of the user's limbs, digits, joints, facial features, head, and/or other body parts.

In some embodiments, the meal detection system 400 includes at least one haptic interface 440 that is suitably configured and operated to provide haptic feedback as an output. The at least one haptic interface 440 generates output(s) that can be experienced by the sense of touch by the user, e.g., mechanical force, vibration, movement, temperature changes, or the like. Haptic feedback generated by the at least one haptic interface 440 may represent or be associated with one or more of the following, without limitation: reminders; alerts; confirmations; notifications; messages; numerical values (such as measurements); status indicators; or any other type of output provided by the meal detection system 400.

In certain embodiments, the user status data (e.g., sensor data) is provided to a gesture recognizer unit or processor. To this end, sensor data may be sent in raw format. Alternatively, a source of sensor data may perform some processing (e.g., filtering, compression, or formatting) on raw sensor data before sending the processed sensor data to the gesture recognizer unit. The gesture recognizer unit analyzes the incoming sensor data and converts the incoming sensor data into a stream of corresponding gestures, which may be predetermined or otherwise classified or categorized. The gesture recognizer unit may use one or more ancillary inputs to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

The output of the gesture recognizer unit—the detected gestures—can be sent to an event detector or processor. The event detector analyzes the incoming stream of gestures to determine if the start of an event of interest (e.g., eating or drinking) has occurred, whether an event is ongoing, whether an event has ended, or the like. For example, if the event detector is implemented as a meal detector intended to capture eating/drinking events, it will be suitably configured to determine if the start of a meal period has occurred, if the user is still consuming a meal, or if the user has stopped eating. Although this description focuses on meal detection, a gesture-based physical behavior detection system may be suitably configured to monitor other types of physical behavior or activities. Such activities include, without limitation: reading; sleeping; smoking; getting dressed; turning down a bed; making a bed; brushing teeth; combing hair; talking on the phone; inhaling or injecting a medication; and activities related to hand hygiene or personal hygiene.

Figure 9:
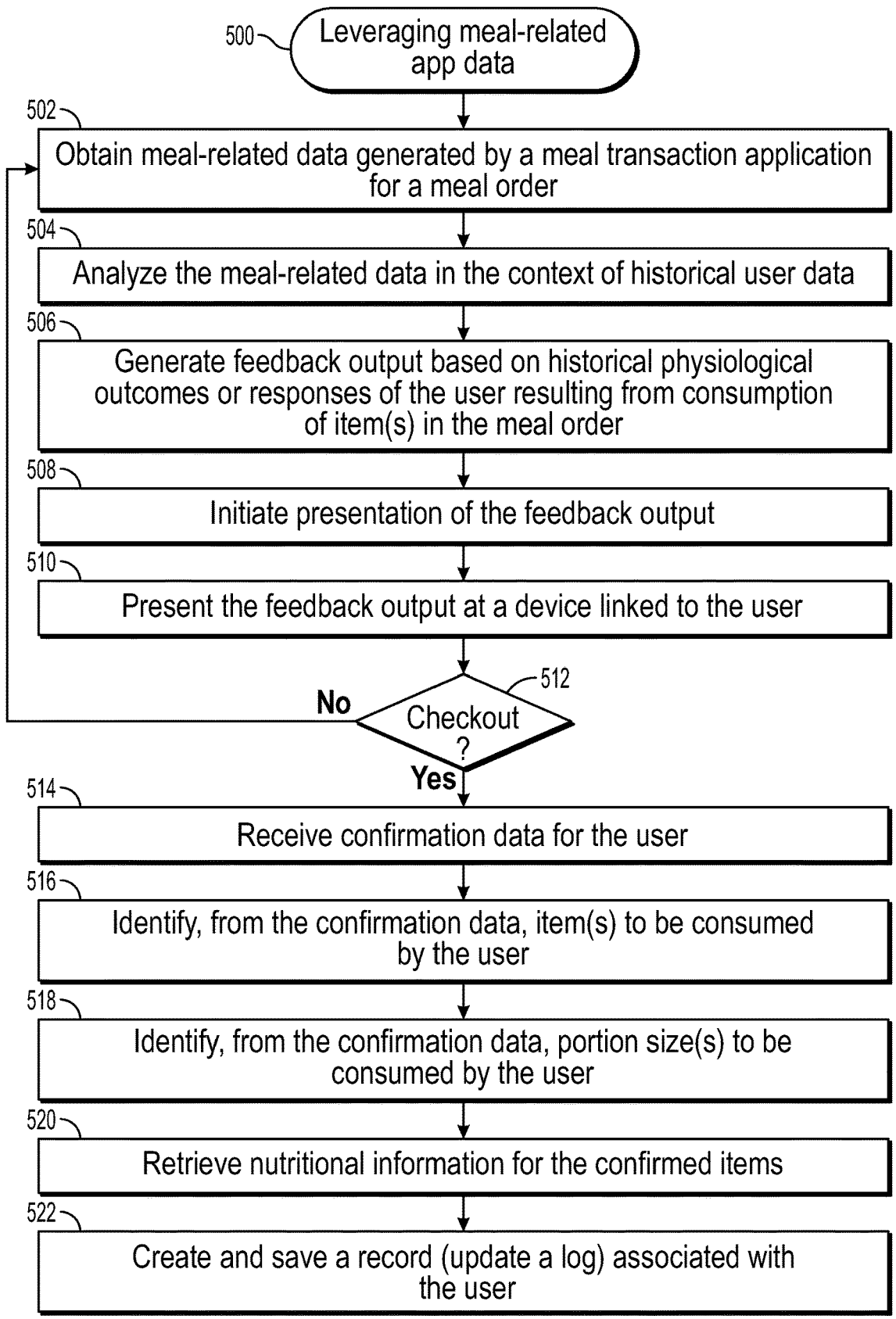
FIG. 9 is a flow chart that illustrates an automated processor-executed method that leverages meal-related data generated by a meal transaction application.
Figure 10:
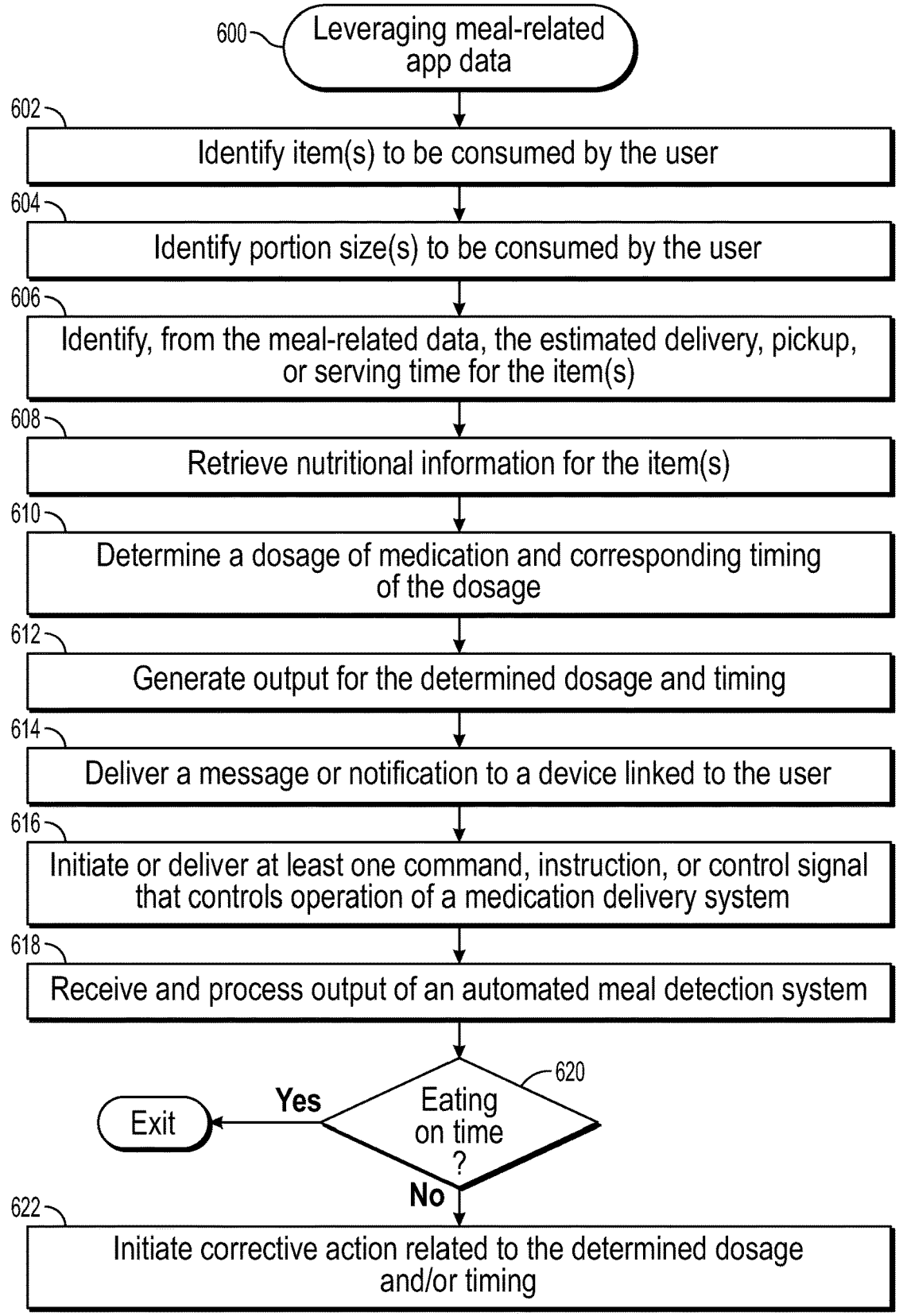
FIG. 10 is a flow chart that illustrates an automated processor-executed method that leverages meal-related data generated by a meal transaction application in the context of a medication delivery system.

Referring again to FIG. 1, the system 100 supports various synergistic features and functions related to operation and use of the meal transaction application 106, particularly in conjunction with the operation of the medication delivery system 102. These synergistic features and functions include, for example: maintaining at least one meal, diet, or food log for the user; calculating medication dosages to be administered by the medication delivery system 102; calculating the timing (e.g., a schedule) for medication dosages to be administered by the medication delivery system 102; and automatically adjusting one or more settings, operating parameters, or therapy-related factors associated with the medication delivery system 102. In this regard, FIGS. 9 and 10 are flow charts that illustrate automated processor-executed methods that leverage meal-related data generated by a meal transaction application. The process 500 depicted in FIG. 9 includes steps associated with making and placing a meal order with the assistance of a meal transaction application. The process 600 depicted in FIG. 10 includes steps associated with the operation of a medication delivery system as informed by certain meal-related data obtained from a meal transaction application.

Referring to FIG. 9, the process 500 obtains meal-related data that is generated by a meal transaction application in response to a meal order for a user (task 502). The meal order may be a delivery order, a pickup order, an advanced order for a meal to be consumed at a restaurant or other location; or a combination thereof. Meal-related data may include any or all of the following, without limitation: a username or identifier of the order-placing user; a username or identifier of each person associated with an ordered item; a name or identifier of each ordered item; the quantity of each ordered item; the price of each ordered item; the total price of the meal; payment information; nutritional information for one or more of the ordered items; an estimated delivery, pickup, or serving time for the meal order (and/or for individual items in the meal order); a name or identifier of the restaurant, store, or vendor of the ordered meal; a delivery address; and contact information of the order-placing user. The meal transaction application may generate and provide meal-related data in an ongoing manner as the items are selected or added to a "shopping cart" for the order. Alternatively, the meal transaction application may generate and provide meal-related data after the meal order is completed (e.g., after selection of a "go to cart" button, a "finished" button, or a "complete my order" button). This example assumes that meal-related data is obtained in an ongoing and quickly updated manner such that the process 500 can react and respond to individual items as they are selected, browsed, or added to the shopping cart. Furthermore, this description assumes that the meal order contains at least one consumable item (food or drink) that is intended for the user. The meal order may, but need not, contain one or more items for people other than the user. For example, the meal order may include various items to feed a family of four, where the user is one member of the family.

In certain embodiments, the process 500 analyzes at least some of the obtained meal-related data prior to completion of the meal order by the meal transaction application (task 504). More specifically, task 504 analyzes meal-related data (for a particular user) in the context of historical user data that has some relationship with user-specific items contained in the meal order. In response to the analyzing, the process 500 generates feedback output based on historical physiological outcomes or responses of the user resulting from previous consumption of one or more of the user-specific items included in the meal order (task 506). Depending on the particular embodiment, the feedback output may include or be realized as a recommendation, a suggestion, an insight, a warning, a notification, a message, or an indication formatted for presentation to the user. The process 500 continues by initiating presentation of the feedback output (task 508), and by presenting the feedback output at a device that is linked to the user (task 510). For example, the feedback output can be presented as a notification, a pop-up message, or an indicator light on a device that is linked to or associated with the user. As another example, the feedback output can be presented in a graphical component or graphical user interface of the meal transaction application.

The automatically generated and presented feedback output informs the user in real-time or near real-time about meal choices and their impact on the user's physiological state or outcome. For example, assume that (1) the user orders or selects a pastrami sandwich from the Stack It High Deli restaurant, (2) the process 500 has access to historical physiological outcomes or response data related to user consumption of that sandwich, and (3) that the user historically experiences higher than normal blood glucose levels after eating that sandwich. The process 500 can generate suitably formatted feedback output in the form of a message such as: "Your glucose usually goes high after you eat this sandwich. Would you like to try something else?" As another example, if the user selects or orders a sugary beverage, the process 500 might generate and present a warning light or a brief pop-up notification in the meal transaction application (with or in close proximity to the graphical user interface that corresponds to the sugary beverage) to warn the user about that choice and/or to recommend ordering a different beverage, such as a diet soda, unsweetened ice tea, or a bottle of water. These and other types of contextually relevant feedback output messages, warnings, and indications are contemplated by this disclosure. The above examples assume that the feedback output is generated and presented in an ongoing manner while the user makes choices or order selections. Alternatively or additionally, feedback output can be generated and presented in response to the user completing a meal order, selecting the "checkout" button, or the like. In other words, the process 500 need not generate or present feedback output on an individual item-by-item basis.

This example assumes that the user completes the meal order by selecting the "checkout" button or an equivalent active element, link, or object rendered by the meal transaction application (the "Yes" branch of query task 512). At checkout, while ordering items that appear in the meal order, or at some time after completion of the order, the process 500 may receive confirmation data for the user (task 514). The confirmation data may represent user-entered data and/or automatically generated data that results from completion of the meal order. In certain embodiments, the confirmation data indicates, flags, or otherwise confirms which items in the meal order are for the specified user (this contemplates the scenario where an ordered meal includes items for a plurality of different people). In certain embodiments, the confirmation data indicates or otherwise confirms a portion size for each item that is ordered for the specified user. In this regard, the portion size may be a percentage of an ordered item that will be consumed or that has actually been consumed. Alternatively or additionally, the portion size may be an estimated weight or volume corresponding to the amount of an ordered item that will be consumed or that has actually been consumed. For example, if the meal order includes a bowl or serving of pasta with meat sauce and the user plans to eat or actually eats only half of the bowl or serving, then the confirmation data may include a 50% value assigned to that particular food item.

The confirmation data allows the system to accurately keep track of the user's food intake for logging purposes and for purposes of regulating medication therapy for the user. Accordingly, the process 500 can identify, from the obtained meal-related data and/or the received confirmation data, at least one item intended to be consumed by the user (task 516). The process 500 can also identify, from the obtained meal-related data and/or the received confirmation data, a portion size (or corresponding portion sizes) for at least one item that is to be consumed by the user (task 518). The identified information can be saved for use with user record-keeping, medication therapy adjustments, or the like.

In certain embodiments, the process 500 retrieves nutritional information for the confirmed or otherwise identified item(s) that are to be consumed by the user (task 520). As mentioned previously, task 520 may involve communication with the restaurant/food database 114 for purposes of obtaining the applicable nutritional information. The user-confirmed items and portion sizes enable the process 500 to obtain or calculate nutritional information that accurately and reliably corresponds to the amount of food or drink that the user actually intends to consume.

The process 500 may continue by creating, saving, or maintaining a record associated with the user, e.g., update a food or diet log (task 522). In this regard, the record may include the identified consumable item(s) and the retrieved nutritional information that corresponds to those identified item(s). The user-specific record can be maintained in a cloud-based database, at a user device, in connection with a mobile app, or the like. See, for example, FIG. 1, which depicts a network accessible diet/food logging database 116 that can be used to store this type of user record.

The example described above assumes that the logging operation occurs in response to a meal order, and before the user consumes the ordered items. It should be understood that the logging operation, including the user confirmation steps mentioned above, may also be performed at a later time, e.g., when the order is delivered, picked up, or served, or just before or after the user has consumed the ordered items. For example, the process 500 can request confirmation from the user regarding which items were actually consumed, and how much was actually consumed (portion size). In certain embodiments, the process 500 receives and processes initial confirmation data (as described above with reference to tasks 514, 516, and 518) and subsequent post-meal confirmation data from the user.

Referring to FIG. 10, the process 600 leverages meal-related data obtained from a meal transaction application in a way that influences the operation of a medication delivery system, such as an insulin infusion device, a manual drug delivery device, a smart pen, or the like. Some of the tasks depicted in FIG. 10 are similar or equivalent to counterpart tasks shown in FIG. 9 and described above. For the sake of brevity and clarity, similar or identical tasks will not be redundantly described in detail in the context of the process 600.

This description assumes that a user has already placed a meal order, using a meal transaction application in the manner described above. Accordingly, the depicted process 600 identifies, from obtained meal-related data and/or received confirmation data, at least one item intended to be consumed by the user (task 602). The process 600 can also identify, from obtained meal-related data and/or received confirmation data, a portion size (or corresponding portion sizes) for at least one item that is to be consumed by the user (task 604). Tasks 602 and 604 are similar to tasks 516 and 518, which were explained above with reference to FIG. 9 and the process 500.

This example assumes that the meal-related data obtained from the meal transaction application includes an estimated delivery time, an estimated pickup time, or an estimated serving time for the item(s) in the meal order. Accordingly, the process 600 identifies, from the obtained meal-related data and/or received confirmation data, an estimated delivery, pickup, or serving time for the item(s) that are to be consumed by the designated user (task 606). The process 600 also retrieves nutritional information for the confirmed or otherwise identified item(s) that are to be consumed by the user (task 608), as described above with reference to task 520 of the process 500.

The process 600 continues by determining a dosage of medication for the user, along with corresponding timing of the dosage (task 610). The timing may indicate a single dosing time, a schedule for a series of dosages, a window of time during which the dosage should be administered, etc. In certain embodiments, the determining considers at least the identified consumable item(s) ordered for the user, the estimated delivery, pickup, or serving time, and the retrieved nutritional information. For example, task 610 may calculate a recommended meal bolus or other dosage of insulin (e.g., a pre-meal and/or post-meal bolus) and at least one suggested insulin dosing time (which may also be influenced by the user's current, historical, and/or predicted glucose level, a measure of active insulin in the body of the user, and other factors).

The process 600 may generate a suitably formatted and configured output for the determined dosage and related timing (task 612), and deliver, render, or otherwise present the output at one or more destination devices. For example, the output could include or be realized as a message or a notification that is deliverable to a device linked to the user (e.g., a smartphone having a patient care application, a medication delivery device such as an insulin pump or a smart insulin pen, a smart pen cap, or a personal computer), wherein the message/notification conveys the determined dosage of medication and the corresponding timing of the dosage. Thus, the process 600 may deliver a message or a notification to a device linked to the user (task 614). This type of message or notification can be used with manual medication delivery methodologies, such as a syringe, a fluid delivery pen, an insulin delivery device, or the like. Alternatively or additionally, the output could include or be realized as at least one command, instruction, or control signal that controls operation of a medication delivery system to administer the determined dosage of medication to the user in accordance with the corresponding timing of the dosage. Thus, the process 600 may initiate or delivery a command, instruction, or control signal that controls operation of one or more medication delivery systems (task 616), such as a user-worn or user-carried insulin infusion pump. In this regard, a medication delivery system can be automatically regulated and controlled without user involvement, or automatically regulated and controlled with mandatory user confirmation or approval actions.

As mentioned above, the calculated dosage of medication and associated timing of the dosage may be influenced by the estimated meal delivery, pickup, or serving time. Ideally, the user will begin eating the ordered items at a time that is close to the estimated delivery, pickup, or serving time. In practice, however, the user may consume the ordered items sooner or later than the estimated time. In some scenarios, the user may order items and forget to eat or delay eating for an extended period of time. In this regard, certain embodiments of the process 600 utilize an automated meal detection system to determine whether the user is eating. Accordingly, the process 600 may receive and process the output of a meal detection system to determine whether the user has started eating or drinking (task 618). The example described here checks for eating/drinking activity occurring within a specified window of time relative to a reference time, e.g., the estimated delivery, pickup, or serving time, the meal ordering time, the actual delivery, pickup, or serving time, or the like. If the output of the meal detection system indicates that the user started eating or drinking within the specified window of time (the "Yes" branch of query task 620), then the process 600 may exit without modifying the calculated dosage of medication or its recommended timing. If, however, the process 600 detects that the user has not started eating or drinking within the specified window of time (the "No" branch of query task 620), then the process 600 initiates corrective action related to the determined dosage of medication and/or the corresponding timing of the dosage (task 622). The corrective action may include or be associated with one or more of the following, without limitation: cancelling or adjusting the timing of the administration of medication; recalculating the dosage of medication; providing a warning, an alert, a notification, or a message to remind the user to consume the ordered item(s) or another food item; adjusting one or more settings, parameters, or variables of the medication delivery system to compensate for the delay; or the like.

As mentioned previously, the meal detection system that provides the information utilized by the process 600 may include or be realized as a gesture-based physical behavior detection system that provides gesture data for the user. In such embodiments, the output processed at task 618 includes the gesture data for the user and/or characterized gesture data that already indicates the occurrence of a detected meal. Thus, the processed gesture data may indicate whether physical behavior of the user corresponds to eating movements, drinking movements, or both.

Alternatively or additionally, the meal detection system may include or be realized as at least one ancillary system that provides ancillary sensor, measurement, or status data. In such embodiments, the output processed at task 618 includes the ancillary sensor, measurement, or status data, which may be characterized to indicate the occurrence of a detected meal. Thus, the processed ancillary data may indicate whether a condition, location, characteristic, or state of the user corresponds to meal consumption. For example, the processed ancillary data may indicate that the user's GPS position corresponds to a frequently visited restaurant at the user's typical lunch time. Such ancillary data, possibly in combination with the output of a gesture-based meal detection system, can be useful to confirm whether or not the user is actually eating or drinking an ordered item.

The various tasks performed in connection with a process disclosed herein may be performed by software, hardware, firmware, or any combination thereof. It should be appreciated that an embodiment of an illustrated process may include any number of additional or alternative tasks, the tasks shown in the figures need not be performed in the illustrated order, and a disclosed process may be incorporated into a more comprehensive procedure or process having additional functionality not described in detail herein. Moreover, one or more of the tasks shown in a figure could be omitted from an embodiment of the depicted process as long as the intended overall functionality remains intact.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method comprising:
obtaining meal-related data generated by a meal transaction application in response to a meal order for a user, the meal-related data comprising an estimated delivery or pickup time for the meal order;
identifying, from the obtained meal-related data, at least one item consumed by or intended to be consumed by the user;
determining a total dosage of insulin to be delivered to the user based on the identified at least one item;
determining a single timing for the delivery of the total dosage of insulin based on the estimated delivery or pickup time for the meal order;
determining, based on physical behavior of the user, whether the user started consuming the at least one item within a predetermined time window;
adjusting the determined total dosage of insulin, the single timing for the delivery of the total dosage of insulin, or a combination thereof, responsive to determining that the user failed to start consuming the at least one item within the predetermined time window; and
delivering, using an insulin delivery device, the determined or adjusted dosage of insulin to the user in accordance with the determined or adjusted timing.

2. The method of claim 1, wherein:
the determining of the total dosage of insulin for the user is based at least in part on the identified at least one item, and nutritional information of the identified at least one item.

3. The method of claim 1, further comprising:
analyzing at least some of the obtained meal-related data prior to completion of the meal order by the meal transaction application;
generating feedback output in response to the analyzing, the feedback output including a recommendation, a suggestion, an insight, a warning, a notification, or an indication, wherein the feedback output is generated based on historical physiological outcomes or responses of the user that results from previous consumption of the at least one item included in the meal order; and
initiating presentation of the feedback output at a device linked to the user.

4. The method of claim 3, further comprising:
presenting the feedback output as the notification, a pop-up message, or an indicator light on the device linked to the user.

5. The method of claim 3, further comprising:
presenting the feedback output in a graphical component of the meal transaction application.

6. The method of claim 1, wherein the identifying comprises:
receiving confirmation data from the user, the confirmation data indicating that the user plans to consume the at least one item.

7. The method of claim 6, wherein the received confirmation data indicates a portion size for the at least one item.

8. A system comprising:
one or more computer-readable storage media comprising program code instructions; and
at least one processor,
wherein the program code instructions are configurable to cause the at least one processor to perform operations comprising:
obtaining meal-related data generated by a meal transaction application in response to a meal order for a user, the meal-related data comprising an estimated delivery or pickup time for the meal order;
identifying, from the obtained meal-related data, at least one item consumed by or intended to be consumed by the user;
determining a total dosage of insulin to be delivered to the user based on the identified at least one item;
determining a single timing for the delivery of the total dosage of insulin based on the estimated delivery or pickup time for the meal order;
determining whether the user started consuming the at least one item within a predetermined time window based on physical behavior of the user;
adjusting the determined total dosage of insulin, the single timing for the delivery of the total dosage of insulin, or a combination thereof, responsive to determining that the user failed to start consuming the at least one item within the predetermined time window; and
delivering, using an insulin delivery device, the determined or adjusted dosage of insulin to the user in accordance with the determined or adjusted timing.

9. The system of claim 8, wherein:
the determining of the total dosage of insulin for the user is based at least in part on the identified at least one item, and nutritional information of the identified at least one item.

10. The system of claim 8, wherein the operations performed by the at least one processor further comprise:
analyzing at least some of the obtained meal-related data prior to completion of the meal order by the meal transaction application;
generating feedback output in response to the analyzing, the feedback output including a recommendation, a suggestion, an insight, a warning, a notification, or an indication, wherein the feedback output is generated based on historical physiological outcomes or responses of the user that results from previous consumption of the at least one item included in the meal order; and
initiating presentation of the feedback output at a device linked to the user.

11. A method comprising:
obtaining meal-related data generated by a meal transaction application in response to a meal order for a user;
identifying, from the obtained meal-related data, at least one item intended to be consumed by the user, and an estimated delivery or pickup time for the meal order;
retrieving nutritional information for the identified at least one item;
determining a total dosage of medication to be delivered to the user based on the identified at least one item and the retrieved nutritional information;
determining a single timing for the delivery of the total dosage of medication based on the estimated delivery or pickup time for the meal order;
determining whether the user started consuming the at least one item within a predetermined time window based on physical behavior of the user;
adjusting the determined total dosage of medication, the single timing for the delivery of the total dosage of medication, or a combination thereof, responsive to determining that the user failed to start consuming the at least one item within the predetermined time window; and
delivering, using a medication delivery system, the determined or adjusted dosage of medication to the user in accordance with the determined or adjusted timing.

12. The method of claim 11, further comprising:
analyzing at least some of the obtained meal-related data prior to completion of the meal order by the meal transaction application;
generating feedback output in response to the analyzing, the feedback output including a recommendation, a suggestion, an insight, a warning, a notification, or an indication, wherein the feedback output is generated based on historical physiological outcomes or responses of the user that results from previous consumption of the at least one item included in the meal order; and
initiating presentation of the feedback output at a device linked to the user.

13. The method of claim 11, wherein determining whether the user started consuming the at least one item within the predetermined time window based on detecting the physical behavior of the user comprises:
processing output of a meal detection system to determine whether the user started consuming the at least one item.

14. The method of claim 13, wherein:
the meal detection system comprises a gesture-based physical behavior detection system;
the processed output comprises gesture data for the user that is provided by the gesture-based physical behavior detection system; and
the gesture data indicates whether the physical behavior of the user corresponds to eating movements, drinking movements, or both eating and drinking movements.

15. The method of claim 13, wherein:
the meal detection system comprises at least one ancillary system;
the processed output comprises ancillary sensor data or status data that is provided by the at least one ancillary system; and
the ancillary sensor data or status data indicates whether a condition, location, characteristic, or state of the user corresponds to meal consumption.

16. The method of claim 11, wherein the identifying comprises:
receiving confirmation data from the user, the confirmation data indicating that the user plans to consume the at least one item.

17. The method of claim 16, wherein the received confirmation data indicates a portion size for the at least one item.

18. A system comprising:
one or more computer-readable storage media comprising program code instructions; and
at least one processor,
wherein the program code instructions are configurable to cause the at least one processor to perform operations comprising:
   obtaining meal-related data generated by a meal transaction application in response to a meal order for a user;
   identifying, from the obtained meal-related data, at least one item intended to be consumed by the user, and an estimated delivery or pickup time for the meal order;
   retrieving nutritional information for the identified at least one item;
   determining a total dosage of medication to be delivered to the user based on the identified at least one item and the retrieved nutritional information;
   determining a single timing for the delivery of the total dosage of medication based on the estimated delivery or pickup time for the meal order;
   determining whether the user started consuming the at least one item within a predetermined time window based on physical behavior of the user;
   adjusting the determined total dosage of medication, the single timing for the delivery of the total dosage of medication, or a combination thereof, responsive to determining that the user failed to start consuming the at least one item within the predetermined time window; and
   delivering, using a medication delivery system, the determined or adjusted dosage of medication to the user in accordance with the determined or adjusted timing.

19. The system of claim 18, wherein the medication delivery system comprises an insulin delivery device, and wherein the determining the total dosage of medication comprises calculating a total dosage of insulin to be administered by the insulin delivery device.

20. The system of claim 18, wherein the operations performed by the at least one processor further comprise:
   analyzing at least some of the obtained meal-related data prior to completion of the meal order by the meal transaction application;
   generating feedback output in response to the analyzing, the feedback output including a recommendation, a suggestion, an insight, a warning, a notification, or an indication, wherein the feedback output is generated based on historical physiological outcomes or responses of the user that results from previous consumption of the at least one item included in the meal order; and
   initiating presentation of the feedback output at a device linked to the user.

21. The system of claim 18, wherein the identifying comprises:
   receiving confirmation data from the user, the confirmation data indicating that the user plans to consume the at least one item.

22. The system of claim 21, wherein the received confirmation data indicates a portion size for the at least one item.

* * * * *